United States Patent
Gregorich

(10) Patent No.: US 10,028,666 B2
(45) Date of Patent: Jul. 24, 2018

(54) PRESSURE SENSING GUIDEWIRE

(71) Applicant: BOSTON SCIENTIFIC SCIMED, INC., Maple Grove, MN (US)

(72) Inventor: Daniel J. Gregorich, Plymouth, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 1000 days.

(21) Appl. No.: 14/196,740

(22) Filed: Mar. 4, 2014

(65) Prior Publication Data

US 2014/0276109 A1    Sep. 18, 2014

Related U.S. Application Data

(60) Provisional application No. 61/788,604, filed on Mar. 15, 2013.

(51) Int. Cl.
| | |
|---|---|
| *A61B 5/0215* | (2006.01) |
| *A61B 5/00* | (2006.01) |
| *A61M 25/09* | (2006.01) |
| A61M 25/00 | (2006.01) |

(52) U.S. Cl.
CPC ........ *A61B 5/02154* (2013.01); *A61B 5/0215* (2013.01); *A61B 5/6851* (2013.01); *A61M 25/09* (2013.01); *A61B 5/6852* (2013.01); *A61M 2025/0002* (2013.01); *A61M 2025/09108* (2013.01); *A61M 2025/09183* (2013.01)

(58) Field of Classification Search
CPC . A61B 5/02154; A61B 5/0215; A61B 5/6852; A61M 2025/0002
See application file for complete search history.

(56) References Cited

U.S. PATENT DOCUMENTS

| | | | |
|---|---|---|---|
| 3,963,323 A | 6/1976 | Arnold | |
| 4,717,718 A * | 1/1988 | Eckenhoff | A61M 31/002 424/438 |
| 4,771,782 A | 9/1988 | Millar | |
| 4,953,553 A | 9/1990 | Tremulis | |
| 5,106,455 A | 4/1992 | Jacobsen et al. | |
| 5,178,159 A | 1/1993 | Christian | |
| 5,238,004 A | 8/1993 | Sahatjian et al. | |
| 5,313,957 A | 5/1994 | Little | |
| 5,421,195 A | 6/1995 | Wlodarczyk | |

(Continued)

FOREIGN PATENT DOCUMENTS

| | | |
|---|---|---|
| DE | 202014100938 U1 | 3/2014 |
| EP | 0235992 A1 | 9/1987 |

(Continued)

*Primary Examiner* — Alyssa M Alter
(74) *Attorney, Agent, or Firm* — Seager, Tufte & Wickhem, LLP

(57) ABSTRACT

Medical devices and methods for making and using medical devices are disclosed. An example medical device includes a pressure sensing guidewire. The pressure sensing guidewire may include a tubular member having a proximal portion and a distal portion. The distal portion may have a plurality of slots formed therein. The distal portion may have a first wall thickness along a first region and a second wall thickness different from the first wall thickness along a second region. A pressure sensor may be disposed within the distal portion of the tubular member.

20 Claims, 11 Drawing Sheets

(56) References Cited

U.S. PATENT DOCUMENTS

| | | |
|---|---|---|
| 5,422,969 A | 6/1995 | Eno |
| 5,427,114 A | 6/1995 | Colliver et al. |
| 5,437,288 A | 8/1995 | Schwartz et al. |
| 5,438,873 A | 8/1995 | Wlodarczyk et al. |
| 5,573,520 A | 11/1996 | Schwartz et al. |
| 5,633,963 A | 5/1997 | Rickenbach et al. |
| 5,755,668 A | 5/1998 | Itoigawa et al. |
| 5,772,609 A | 6/1998 | Nguyen et al. |
| 5,797,856 A | 8/1998 | Frisbie et al. |
| 5,836,885 A | 11/1998 | Schwager |
| 5,872,879 A | 2/1999 | Hamm |
| 5,902,248 A | 5/1999 | Millar et al. |
| 5,916,177 A | 6/1999 | Schwager |
| 5,938,624 A | 8/1999 | Akerfeldt et al. |
| 5,949,929 A | 9/1999 | Hamm |
| 6,112,598 A | 9/2000 | Tenerz et al. |
| 6,120,457 A | 9/2000 | Coombes et al. |
| 6,139,510 A | 10/2000 | Palmero |
| 6,162,182 A | 12/2000 | Cole |
| 6,167,763 B1 | 1/2001 | Tenerz et al. |
| 6,196,980 B1 | 3/2001 | Akerfeldt et al. |
| 6,248,083 B1 | 6/2001 | Smith et al. |
| 6,265,792 B1 | 7/2001 | Granchukoff |
| 6,394,986 B1 | 5/2002 | Millar |
| 6,398,738 B1 | 6/2002 | Millar |
| 6,409,677 B1 | 6/2002 | Tulkki |
| 6,428,336 B1 | 8/2002 | Akerfeldt |
| 6,508,803 B1 | 1/2003 | Horikawa et al. |
| 6,565,514 B2 | 5/2003 | Svanerudh et al. |
| 6,579,246 B2 | 6/2003 | Jacobsen et al. |
| 6,585,660 B2 | 7/2003 | Dorando et al. |
| 6,615,067 B2 | 9/2003 | Hoek et al. |
| 6,663,570 B2 | 12/2003 | Mott et al. |
| 6,766,720 B1 | 7/2004 | Jacobsen et al. |
| 6,767,327 B1 | 7/2004 | Corl et al. |
| 6,776,720 B2 | 8/2004 | Bartlett |
| 6,908,442 B2 | 6/2005 | Von Malmborg et al. |
| 6,918,882 B2 | 6/2005 | Skujins et al. |
| 6,918,873 B1 | 7/2005 | Millar et al. |
| 6,974,422 B1 | 12/2005 | Millar |
| 6,976,965 B2 | 12/2005 | Carl et al. |
| 6,993,974 B2 | 2/2006 | Tenerz et al. |
| 6,994,695 B1 | 2/2006 | Millar |
| 7,071,197 B2 | 7/2006 | Leonardi et al. |
| 7,134,994 B2 | 11/2006 | Alpert et al. |
| 7,162,926 B1 | 1/2007 | Guziak et al. |
| 7,187,453 B2 | 3/2007 | Belleville |
| 7,259,862 B2 | 8/2007 | Duplain et al. |
| 7,265,847 B2 | 9/2007 | Duplain et al. |
| 7,274,956 B2 | 9/2007 | Mott et al. |
| 7,331,236 B2 | 2/2008 | Smith et al. |
| 7,532,920 B1 | 5/2009 | Ainsworth |
| 7,618,379 B2 | 11/2009 | Reynolds et al. |
| 7,684,657 B2 | 3/2010 | Donlagic et al. |
| 7,689,071 B2 | 3/2010 | Belleville et al. |
| 7,715,903 B2 | 5/2010 | Hartley et al. |
| 7,724,148 B2 | 5/2010 | Samuelsson et al. |
| 7,731,664 B1 | 6/2010 | Millar |
| 7,759,633 B2 | 7/2010 | Duplain et al. |
| 7,783,338 B2 * | 8/2010 | Ainsworth ............ A61B 5/0084 600/300 |
| 7,878,984 B2 | 2/2011 | Davis et al. |
| 7,930,014 B2 | 4/2011 | Huenneckens et al. |
| 7,946,997 B2 | 5/2011 | Hübinette |
| 8,025,623 B1 | 9/2011 | Millar |
| 8,029,447 B2 | 10/2011 | Kanz et al. |
| 8,174,395 B2 | 5/2012 | Samuelsson et al. |
| 8,216,151 B2 | 7/2012 | Smith |
| 8,298,156 B2 | 10/2012 | Manstrom et al. |
| 8,317,715 B2 | 11/2012 | Belleville et al. |
| 8,343,076 B2 | 1/2013 | Sela et al. |
| 8,393,802 B2 | 3/2013 | Stanley et al. |
| 8,410,940 B2 | 4/2013 | Samuelsson et al. |
| 8,461,997 B2 | 6/2013 | Samuelsson et al. |
| 8,485,985 B2 | 7/2013 | Manstrom et al. |
| 8,555,712 B2 | 10/2013 | Narvaez et al. |
| 8,556,820 B2 | 10/2013 | Alpert et al. |
| 8,562,537 B2 | 10/2013 | Alpert et al. |
| 8,583,218 B2 | 11/2013 | Eberle |
| 8,636,659 B2 | 1/2014 | Alpert et al. |
| 8,641,633 B2 | 2/2014 | Smith |
| 8,641,639 B2 | 2/2014 | Manstrom et al. |
| 8,676,299 B2 | 3/2014 | Schmitt et al. |
| 8,698,638 B2 | 4/2014 | Samuelsson et al. |
| 8,752,435 B2 | 6/2014 | Belleville et al. |
| 8,936,401 B2 | 1/2015 | Belleville et al. |
| 8,998,823 B2 | 4/2015 | Manstrom et al. |
| 9,052,466 B2 | 6/2015 | Belleville et al. |
| 2002/0013527 A1* | 1/2002 | Hoek .................. A61B 5/0031 600/437 |
| 2003/0069522 A1 | 4/2003 | Jacobsen et al. |
| 2004/0073141 A1 | 4/2004 | Hartley et al. |
| 2004/0181174 A2 | 9/2004 | Davis et al. |
| 2005/0000294 A1 | 1/2005 | Tenerz et al. |
| 2006/0122537 A1 | 6/2006 | Reynolds et al. |
| 2008/0119758 A1 | 5/2008 | Samuelsson et al. |
| 2009/0082678 A1 | 3/2009 | Smith |
| 2009/0192412 A1 | 7/2009 | Sela et al. |
| 2010/0145308 A1 | 6/2010 | Layman et al. |
| 2010/0241008 A1 | 9/2010 | Belleville et al. |
| 2011/0071407 A1 | 3/2011 | Hübinette et al. |
| 2011/0178413 A1* | 7/2011 | Schmitt ................ A61B 5/0066 600/478 |
| 2011/0186294 A1 | 8/2011 | Narvaez et al. |
| 2011/0319773 A1 | 12/2011 | Kanz et al. |
| 2012/0227505 A1 | 9/2012 | Belleville et al. |
| 2012/0265102 A1 | 10/2012 | Leo et al. |
| 2013/0051731 A1 | 2/2013 | Belleville et al. |
| 2013/0218032 A1 | 8/2013 | Belleville |
| 2013/0296718 A1* | 11/2013 | Ranganathan .......... A61B 5/02 600/481 |
| 2013/0317372 A1 | 11/2013 | Eberle et al. |
| 2014/0005558 A1 | 1/2014 | Gregorich |
| 2014/0058275 A1 | 2/2014 | Gregorich et al. |
| 2014/0081244 A1 | 3/2014 | Voeller et al. |
| 2014/0107624 A1 | 4/2014 | Belleville |
| 2014/0121475 A1 | 5/2014 | Alpert et al. |
| 2014/0241669 A1 | 8/2014 | Belleville et al. |
| 2014/0248021 A1 | 9/2014 | Belleville et al. |
| 2015/0301288 A1 | 10/2015 | Thornton, Jr. |

FOREIGN PATENT DOCUMENTS

| | | |
|---|---|---|
| EP | 0738495 A1 | 10/1996 |
| EP | 0879615 A1 | 11/1998 |
| EP | 0879617 A1 | 11/1998 |
| EP | 1479407 A1 | 11/2004 |
| EP | 1927316 A1 | 6/2008 |
| JP | 08-280634 A | 10/1996 |
| JP | 08257128 A | 10/1996 |
| JP | 10-337280 A | 12/1998 |
| JP | 11-502131 A | 2/1999 |
| JP | 11-508160 A | 7/1999 |
| JP | 2010-512857 A | 4/2010 |
| JP | 2012-520690 A | 9/2012 |
| WO | 9313707 A1 | 7/1993 |
| WO | 9533983 A1 | 12/1995 |
| WO | 9626671 A1 | 9/1996 |
| WO | 9700641 A1 | 1/1997 |
| WO | 9945352 A1 | 9/1999 |
| WO | 2008034010 A2 | 3/2008 |
| WO | 2008076931 A2 | 6/2008 |
| WO | 2010105356 A1 | 9/2010 |
| WO | 2011027282 A1 | 3/2011 |
| WO | 2011090744 A2 | 7/2011 |
| WO | 2011123689 A1 | 10/2011 |
| WO | 2012000798 A1 | 1/2012 |
| WO | 2012/061935 A1 | 5/2012 |
| WO | 2012090210 A1 | 7/2012 |
| WO | 2013033489 A1 | 3/2013 |
| WO | 2014025255 A1 | 2/2014 |

* cited by examiner

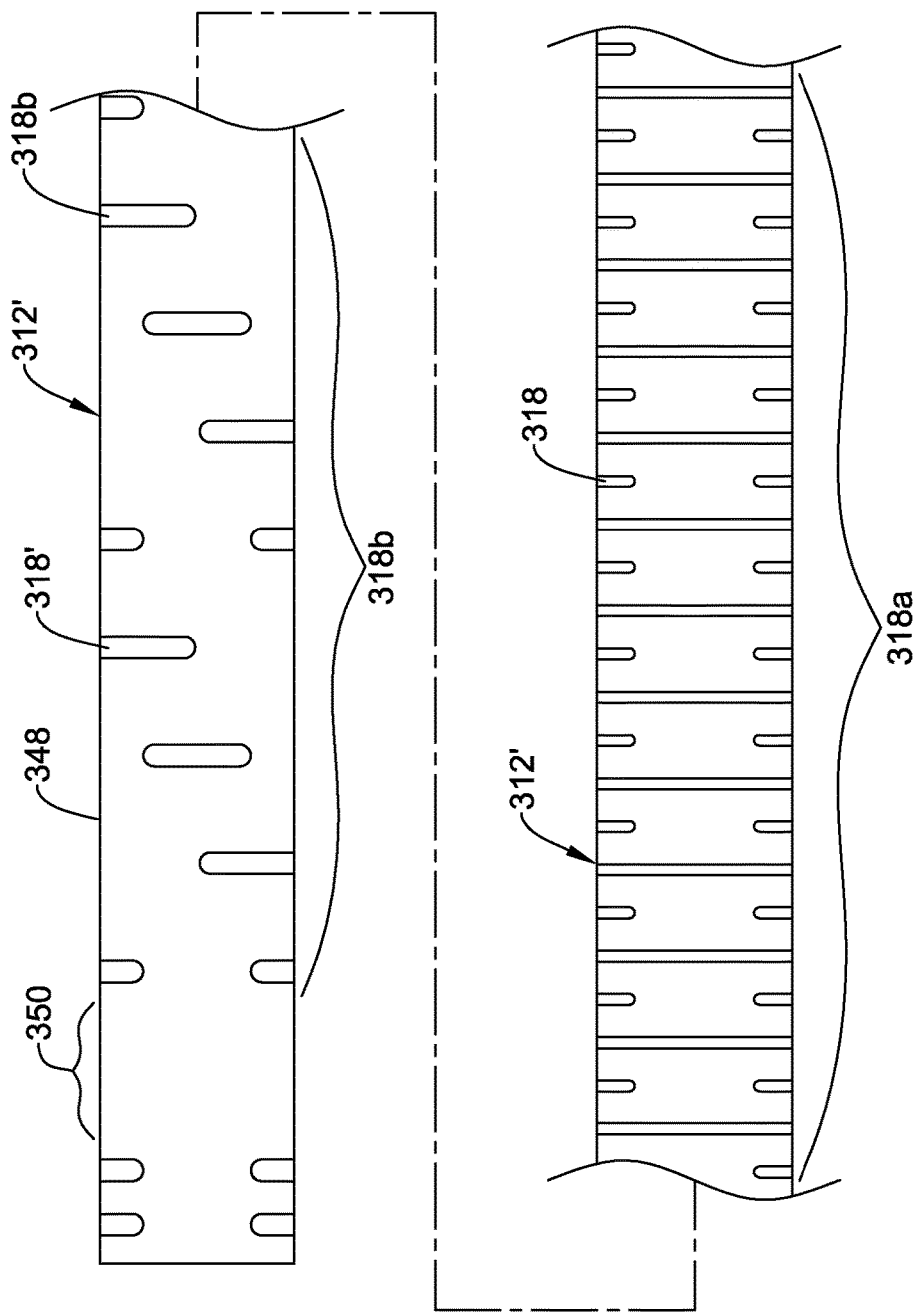

PRESSURE SENSING GUIDEWIRE

CROSS-REFERENCE TO RELATED APPLICATIONS

This application claims priority under 35 U.S.C. § 119 to U.S. Provisional Application Ser. No. 61/788,604, filed Mar. 15, 2013, the entirety of which is incorporated herein by reference.

TECHNICAL FIELD

The present disclosure pertains to medical devices, and methods for manufacturing medical devices. More particularly, the present disclosure pertains to blood pressure sensing guidewires.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes a pressure sensing guidewire. The pressure sensing guidewire may include a shaft having a proximal portion, a distal portion, and a distal tip portion. The distal portion may have a plurality of slots formed therein. A pressure sensor may be disposed within the distal portion of the shaft.

Another example pressure sensing guidewire may include a tubular member having a proximal portion, a distal portion, and a lumen defined therein. The distal portion may have a plurality of slots formed therein. The plurality of slots may be configured to allow fluid to flow from an outer surface of the tubular member, through the slots, and into the lumen. A pressure sensor may be disposed within the lumen of the tubular member and may be positioned within the distal portion of the tubular member. A tip member may be coupled to the distal portion of the tubular member.

A pressure sensing guidewire system is also disclosed. The pressure sensing guidewire system may include a tubular member having a proximal portion, a slotted portion, and a lumen defined therein. The slotted portion may have a plurality of slots formed therein. The plurality of slots may be configured to allow fluid to flow from an outer surface of the tubular member, through the slots, and into the lumen. An optical pressure sensor may be disposed within the lumen of the tubular member and may be positioned within the distal portion of the tubular member. A fiber optic cable may be attached to the optical pressure sensor and may extend proximally therefrom. A handle member may be coupled to the proximal portion of the tubular member and the fiber optic cable. The system may also include an interferometer and a cable extending between the handle member and the interferometer.

Another example pressure sensing guidewire may include a tubular member having a proximal portion and a distal portion. The distal portion may have a plurality of slots formed therein. The distal portion may have a first wall thickness along a first region and a second wall thickness different from the first wall thickness along a second region. A pressure sensor may be disposed within the distal portion of the tubular member.

Another example pressure sensing guidewire may include a tubular member having a proximal portion, a distal portion, and a lumen defined therein. The distal portion may have a first region having a first wall thickness and a second region with a second wall thickness that is larger than the first wall thickness. The distal portion may have a plurality of slots formed therein. At least some of the slots disposed along the first region may have an increased slot width relative to slots disposed along the second region. The first region may include a landing area that is free of slots. A pressure sensor may be disposed along the first region and may be positioned adjacent to the landing area.

An example method for manufacturing a pressure sensing guidewire may include providing a tubular member having a proximal portion, a distal portion, and a lumen defined therein. The method may also include drilling the distal portion of the tubular member so as to define a thinned wall region having a reduced wall thickness, forming a plurality of slots in the distal portion, and disposing an optical pressure sensor along the thinned wall region of the distal portion.

Another example pressure sensing guidewire may include a tubular member having a proximal portion, a distal portion, and a lumen defined therein. The distal portion may include a housing region having an increased inner diameter relative to proximal portion of the tubular member. The distal portion may have a plurality of slots formed therein. At least some of the slots disposed along the housing region have an increased slot width relative to slots disposed along other sections of the distal portion of the tubular member. The housing region may include a landing area that is free of slots. A pressure sensor may be disposed along the housing region and positioned adjacent to the landing area.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 12 is a perspective view of an example tubular member.

Figure 1:
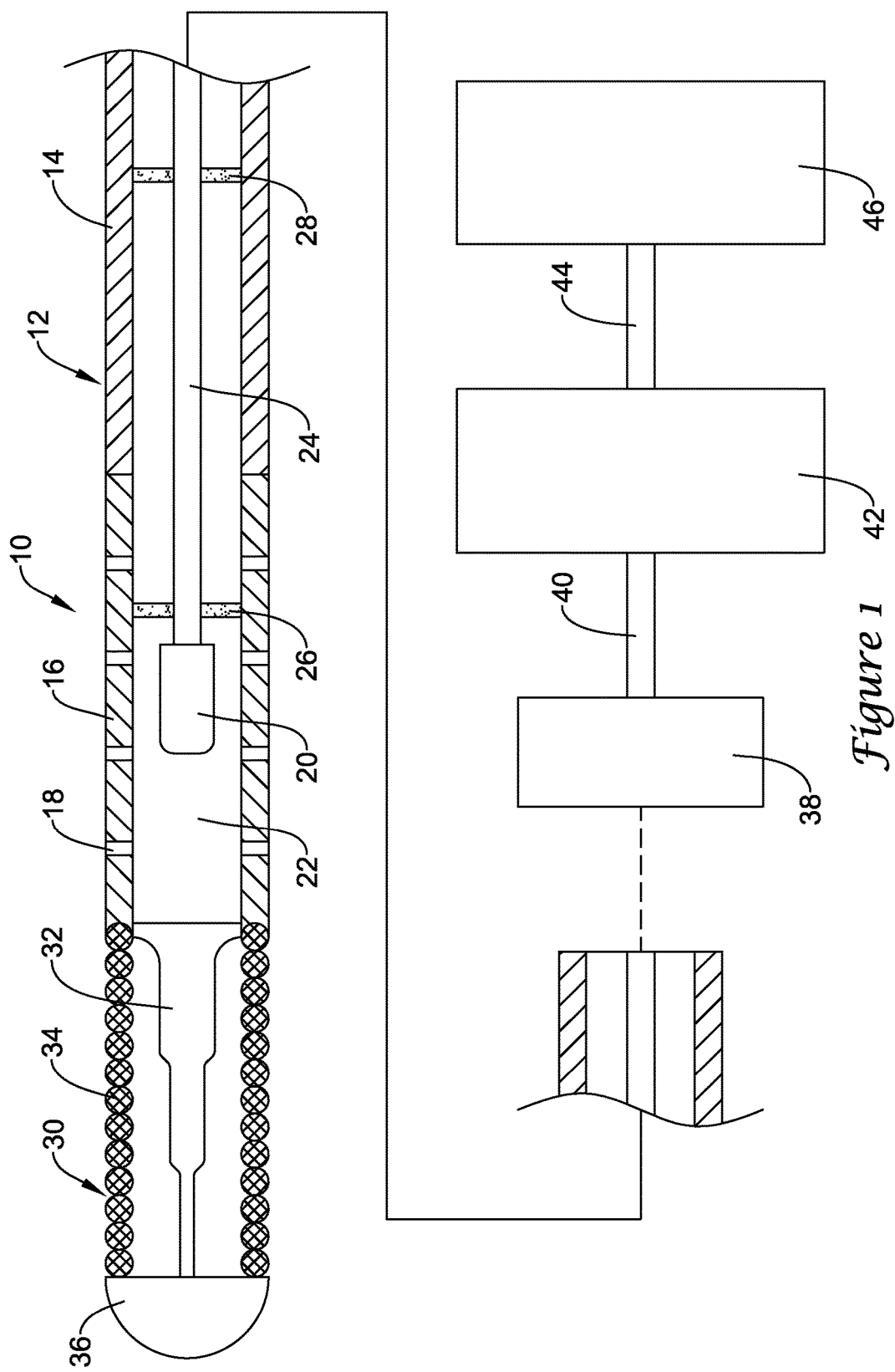
FIG. 1 is a partial cross-sectional side view of a portion of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as the pressure after a stenosis relative to the pressure before the stenosis. A number of pressure sensing devices, however, may pose technical challenges for steering, tracking, torqueing or otherwise navigating the device within the vasculature. For example, medical devices may include a relatively stiff pressure sensor located at or near the distal tip of the device and/or a sensor housing (in which the sensor is mounted) that may also be relatively stiff. Disclosed herein are a number of medical device that include pressure sensing capabilities and may be more easily steered, tracked, torqued, and/or otherwise navigated through the anatomy.

FIG. 1 illustrates a portion of an example medical device 10. In this example, medical device 10 is a blood pressure sensing guidewire 10. However, this is not intended to be limiting as other medical devices are contemplated including, for example, catheters, shafts, leads, wires, or the like. Guidewire 10 may include a guidewire shaft or tubular member 12. Tubular member 12 may include a proximal portion 14 and a distal portion 16. In some embodiments, proximal portion 14 and distal portion 16 are simply portions of the same monolith of material. In other embodiments, proximal portion 14 and distal portion 16 are discrete members that are attached to one another using a suitable attachment process (e.g., solder, weld, adhesive, or the like).

A plurality of slots 18 may be formed in tubular member 12. In at least some embodiments, slots 18 are formed in distal portion 16. In at least some embodiments, proximal portion 14 lacks slots 18. However, proximal portion 14 may include slots 18. Slots 18 may be desirable for a number of reasons. For example, slots 18 may provide a desirable level of flexibility to tubular member 12 (e.g., along distal portion 16) while also allowing suitable transmission of torque.

A pressure sensor 20 may be disposed within tubular member 12 (e.g., within a lumen 22 of tubular member 12). While pressure sensor 20 is shown schematically in FIG. 1, it can be appreciated that the structural form and/or type of pressure sensor 20 may vary. For example, pressure sensor 20 may include a semiconductor (e.g., silicon wafer) pressure sensor, piezoelectric pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor.

Typically, pressure sensors in guidewires are mounted within a mount or mounting structure at the distal end of the guidewire. The mount may take the form of a hypotube with a side hole or opening formed therein that provides access for the blood to reach the pressure sensor. Because the pressure sensor itself may be somewhat rigid and/or stiff and because the mount may also be somewhat rigid and/or stiff, such a configuration may define a region with increased stiffness at or near the distal end of the guidewire. This could pose technical challenges for navigating the guidewire within the vasculature.

The use of tubular member 12 (e.g., distal portion 16 having slots 18 formed therein) may improve the overall flexibility profile of guidewire 10 and/or improve the navigation, steerability, and trackability of guidewire 10. For example, the flexibility of distal portion 16 may be reduced when compared to a typical hypotube pressure sensor mount. Furthermore, the design of distal portion 16 can be tailored to provide a flexibility profile suitable for a given guidewire/intervention through a variety of different patterns and/or configurations for slots 18. Numerous slot configurations are contemplated including those disclosed herein.

Moreover, slots 18 may define a fluid pathway that allows blood (and/or a body fluid) to flow from a position along the exterior or outer surface of guidewire 10 (and/or tubular member 12), through slots 18, and into the lumen 22 of tubular member 12, where the blood can come into contact with pressure sensor 20. Because of this, no additional side openings/holes (e.g., other than slots 18) may be necessary in tubular member 12 for pressure measurement. This may also allow the length of distal portion 16 to be shorter than typical sensor mounts or hypotubes that would need to have a length sufficient for a suitable opening/hole (e.g., a suitable "large" opening/hole) to be formed therein that provides fluid access to sensor 20.

In use, a clinician may use guidewire 10 to measure or calculate FFR (e.g., the pressure after an intravascular lesion relative to the pressure before the lesion). This may include taking an initial pressure reading before or upstream of the lesion and then a comparative reading after or downstream of the lesion. This may also include monitoring the pressure while advancing guidewire 10 through a blood vessel until a pressure differential or drop in pressure is observed, indicating that guidewire 10 has reached and/or partially past the lesion as well as monitoring increases in pressure during and/or following a treatment intervention. In some embodiments, a second pressure measuring device may be used to measure pressure at another intravascular location and this pressure may be utilized in the calculation of FFR or otherwise used as part of the intervention.

As indicated above, pressure sensor 20 may include an optical pressure sensor. In at least some of these embodiments, a fiber optic cable 24 is attached to pressure sensor 20 and extends proximally therefrom. An attachment member 26 may attach fiber optic cable 24 to tubular member 12. Attachment member 26 may be circumferentially disposed about and attached to fiber optic 24 and be secured to the inner surface of tubular member 12 (e.g., distal portion 16). In at least some embodiments, attachment member 26 is proximally spaced from pressure sensor 20. Other arrangements are contemplated.

In at least some embodiments, a sealing member 28 may be disposed within tubular member 12. Sealing member 28 may be generally configured to seal or otherwise prevent body fluids that enter lumen 22 (e.g., through slots 18) from passing through tubular member 12 to more proximal regions of guidewire 10 (including the proximal end of guidewire 10 and/or outside the patient). Sealing member 28 may be positioned at a suitable location along tubular member. This may include being positioned proximal of slots 18. While a single sealing member 28 is illustrated, additional sealing members 28 may also be utilized and the additional sealing members 28 may be positioned at a suitable location along tubular member 12.

A tip member 30 may be coupled to tubular member 12. The precise form of tip member 30 can vary. For example, tip member may include a core member 32, a spring or coil 34, and a tip 36. Core member 32 may include one or more tapers. Core member 32 and/or coil 34 may be attached to tubular member 12 using a suitable attachment technique such as soldering, thermal bonding, welding, adhesive, or the like. Tip 36 may be a solder ball tip. Other tips are contemplated. In some embodiments, tip 36 may be secured directly to tubular member 12. According to these embodiments, core member 32 and/or coil 34 may be omitted from tip member 30 and/or guidewire 10.

The proximal end of guidewire 10 may be configured to attach to a connector or handle member 38. Handle 38 may include a suitable connector for a cable 40 to attached thereto and extend to another suitable device such as a signal conditioner or interferometer 42. Another cable 44 may extend from signal conditioner 42 to a suitable output device or display and/or monitoring unit 46. A clinician may utilize the readings from the display device 46 to tailor the intervention to the needs of the patient or otherwise advance the goals of the intervention. These are just examples. Other devices and/or arrangements may be utilized with guidewire 10.

Figure 2:
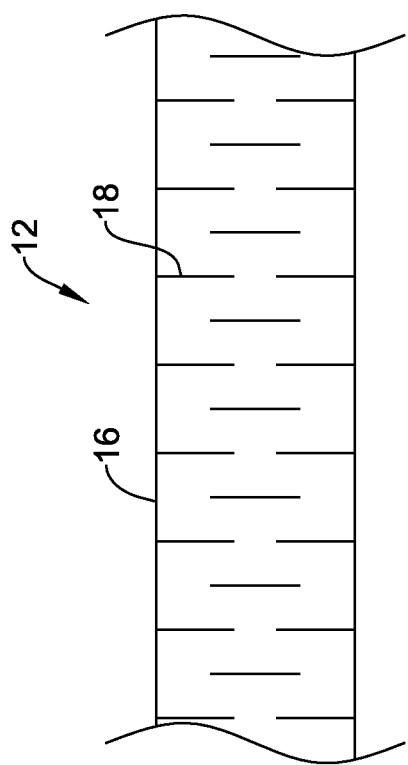
FIG. 2 is a side view of a portion of an example tubular member.
Figure 3:
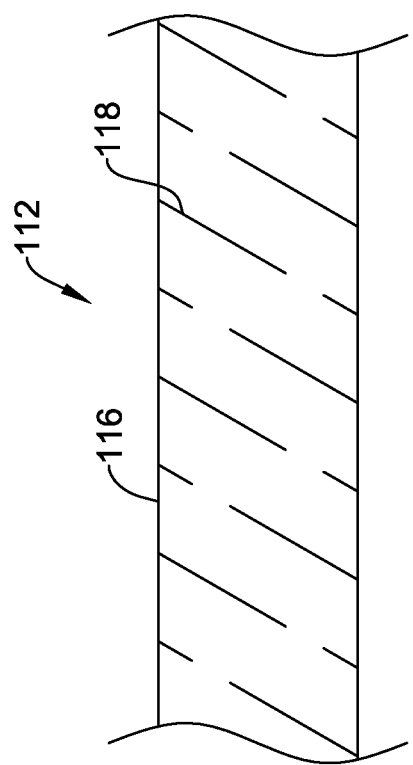
FIG. 3 is a side view of a portion of another example tubular member.

FIG. 2 illustrates distal portion 16 of tubular member 12. Here it can be seen that at least some of slots 18 may lie in a plane transverse to a longitudinal axis of tubular member 12. In this example, slots 18 are arranged in groups of opposed pairs of slots 18. Subsequent opposed pairs of slots 18 may be rotated (e.g., 90 degrees as shown or any other suitable angle). Numerous other arrangements are contemplated. For example, FIG. 3 illustrates distal portion 116 of another example tubular member 112. Here it can be seen that at least some of the slots 118 are arranged into a pattern defining an interrupted helix. These are just examples. Numerous other patterns and/or slot configurations are contemplated including those disclosed herein.

Figure 4:
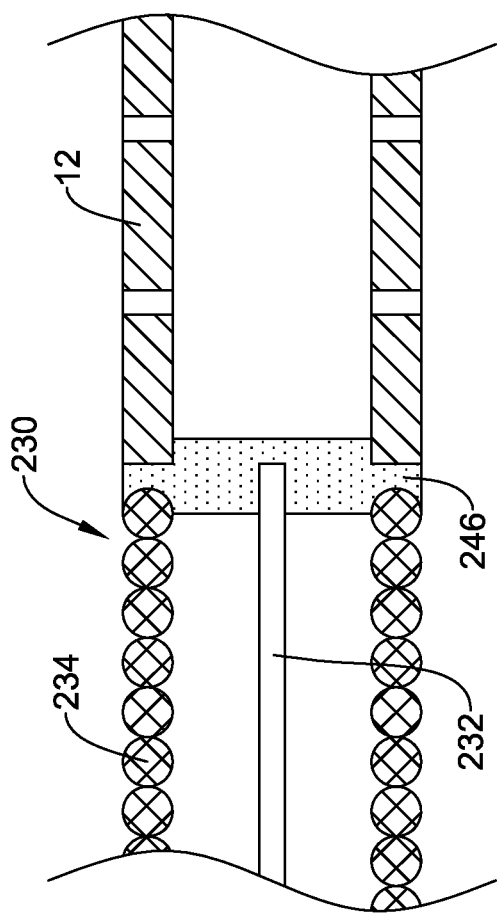
FIG. 4 is a cross-sectional side view of a portion of another example medical device.

FIG. 4 illustrates a portion of another example tip member 230 that may be used with guidewire 10 (and/or other guidewires disclosed or otherwise contemplated herein). Tip member 230 may include a shaping ribbon 232 and a coil 234. Shaping ribbon 232 may be formed from a shapeable material such as, for example, stainless steel, linear elastic nitinol, other materials disclosed herein, or the like. Shaping ribbon 232 and/or coil 234 may be attached to tubular member 12 with a bonding member 246. Bonding member 246 may include an adhesive, solder, or the like, or other suitable bonding members.

Figure 5:
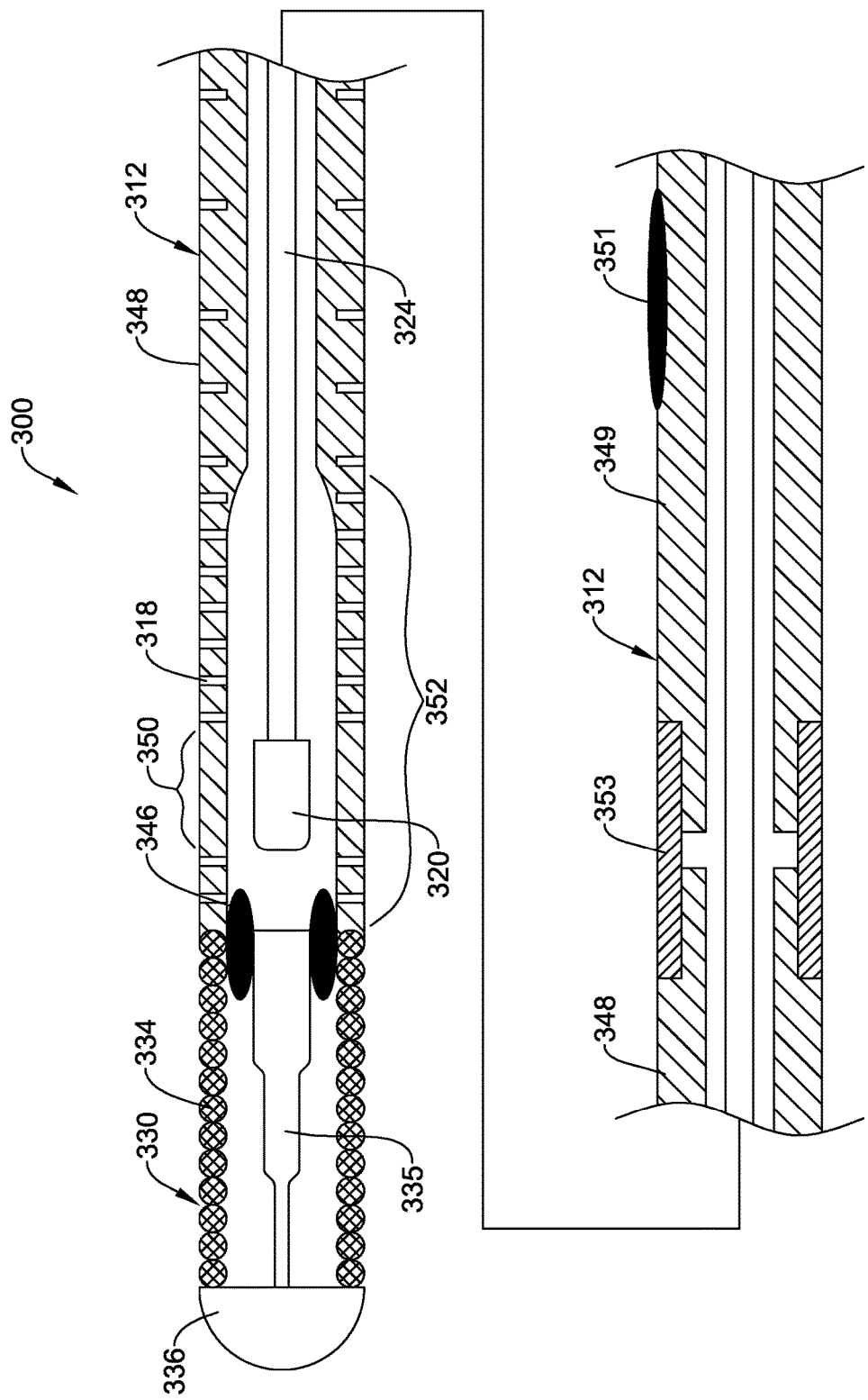
FIG. 5 is a partial cross-sectional side view of a portion of another example medical device.

FIG. 5 illustrates another example medical device 300, taking the form of pressure sensing guidewire, that may be similar in form and function to other devices/guidewire disclosed herein. Guidewire 300 may include a tubular member 312 having a proximal portion 349 and a distal portion 348. In some embodiments, proximal portion 349 and distal portion 348 are formed from the same monolith of material. In other words, proximal portion 349 and distal portion 348 are portions of the same tube defining tubular member 312. In other embodiments, proximal portion 349 and distal portion 348 are separate tubular members that are joined together. For example, a section of the outer surface of portions 349/348 may be removed and a sleeve 353 may be disposed over the removed sections to join portions 349/348. Alternatively, sleeve 353 may be simply disposed over portions 349/348. Other bonds may also be used including welds, thermal bonds, adhesive bonds, or the like.

The materials for proximal portion 349 and distal portion 348 may vary and may include those materials disclosed herein. For example, distal portion 348 may include a nickel-cobalt-chromium-molybdenum alloy (e.g., MP35-N). Proximal portion 349 may include stainless steel. These are just examples. Other materials may also be utilized. If included, sleeve 351 used to join proximal portion 349 with distal portion 348 may include a material that desirably bonds with both proximal portion 349 and distal portion 348. For example, sleeve 351 may include a nickel-chromium-molybdenum alloy (e.g., INCONEL).

Tubular member 312 may include a hydrophilic coating 353 (on a portion of which is shown in FIG. 5). In some embodiments, hydrophilic coating 353 may extend along substantially the full length of tubular member 312. In other embodiments, one or more discrete sections of tubular member 312 may include hydrophilic coating 353.

Distal portion 348 may have a plurality of slots 318 formed therein. The slots 318 may be arranged/distributed along distal portion 348 in a suitable manner including any of those arrangements disclosed herein. For example, slots 318 may be arranged as opposing pairs of slots 318 that are distributed along the length of distal portion 348. In some embodiments, adjacent pairs of slots 318 may have a substantially constant spacing relative to one another. Alternatively, the spacing between adjacent pairs may vary. For example, more distal regions of distal portion 318 may have a decreased spacing (and/or increased slot density), which may provide increased flexibility. In other embodiments, more distal regions of distal portion 318 may have an increased spacing (and/or decreased slot density). Other arrangements are contemplated.

In some embodiments, proximal portion 349 may also include slots 318. According to these embodiments, the slots 318 in proximal portion 349 may be arranged in a suitable manner include those disclosed herein. In other embodiments, proximal portion 349 may be substantially free of slots 318.

A tip member 330 may be coupled to distal portion 348. Tip member 330 may be similar to other tips/tip members disclosed herein. For example, tip member 330 may include a spring or coil member 334. A distal tip 336 may be attached to spring 334. In at least some embodiments, tip 336 may take the form of a solder ball tip. Tip member 330 may also include a shaping member 335. Tip member 330 may be joined to distal portion 348 of tubular member 312 with a bonding member 346 such as a weld.

In at least some embodiments, distal portion 348 may include a region with a thinned wall and/or an increased inner diameter that defines a housing region 352. In general, housing region 352 is the region of distal portion 348 that ultimately "houses" the pressure sensor (e.g., a pressure sensor 320). By virtue of having a portion of the inner wall of tubular member 312 being removed at housing region 352, additional space may be created or otherwise defined that can accommodate sensor 320.

As indicated above, pressure sensor 320 may be disposed within housing region 352. In at least some embodiments, pressure sensor 320 may be an optical (and/or fabry-perot) pressure sensor similar to other pressure sensors disclosed herein. An optical fiber 324 may be attached to pressure sensor 320 and extend proximally therefrom. At its proximal end (not shown) optical fiber 324 may connect to a suitable processing device (e.g., signal processing unit, interferometer, or the like). In some of these and in other embodiments, an intermediate or adapter cable may be connected to the proximal end of guidewire 300 (and optical fiber 324), which, in turn, connects to a suitable processing unit.

In at least some embodiments, it may be desirable for pressure sensor 320 to have reduced exposure along its side surfaces to fluid pressure (e.g., from the blood). Accordingly, it may be desirable to position pressure sensor 320 along a landing region 350 defined along housing region 352. Landing region 350 may be substantially free of slots 318 so that the side surfaces of pressure sensor 320 have a reduced likelihood of being deformed due to fluid pressures at these locations. Distal of landing are 350, housing region 352 may include slots 318 that provide fluid access to pressure sensor 320.

Figure 6:
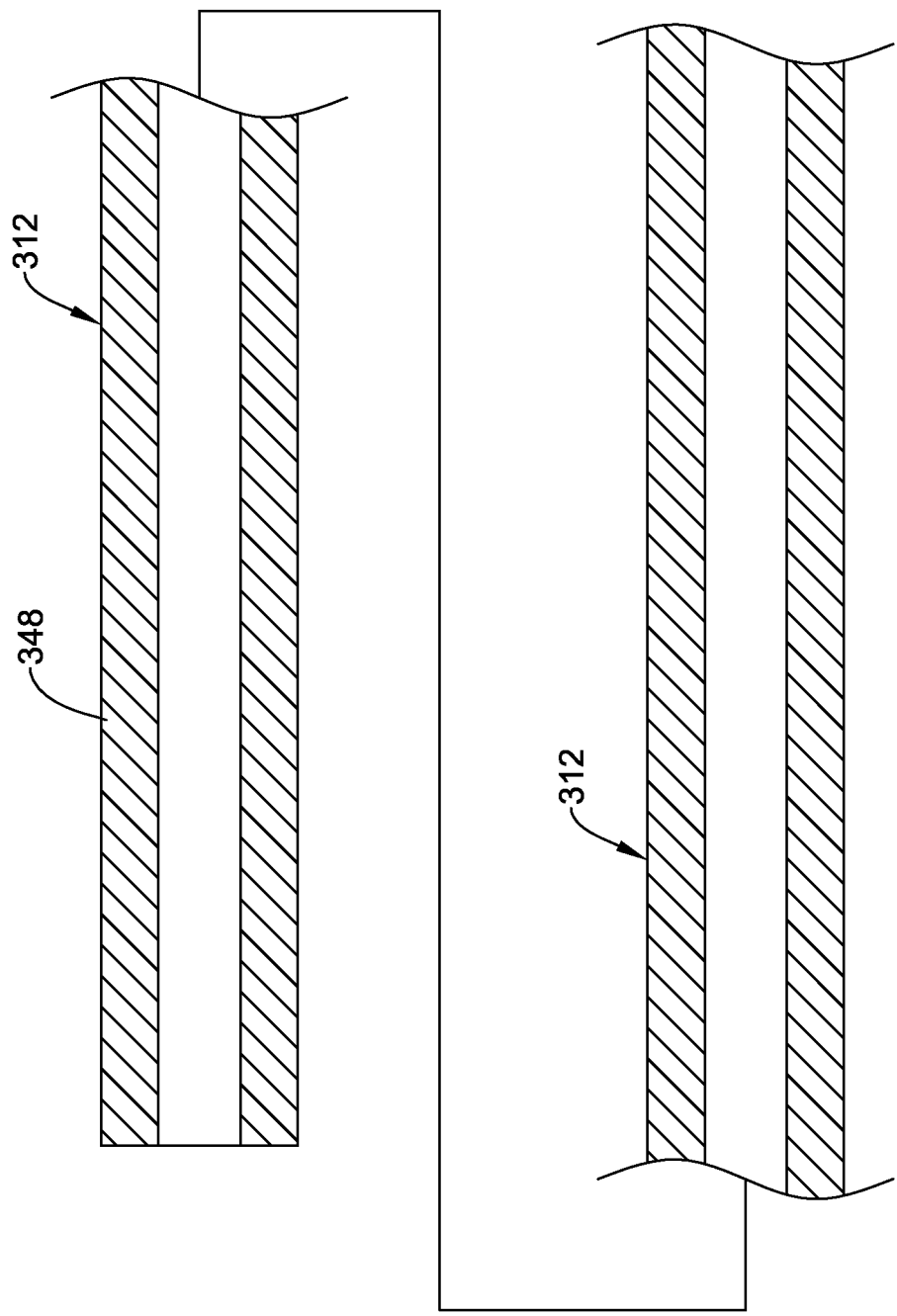
FIGS. 6-10 illustrate a portion of an example method for manufacturing an example medical device.
Figure 7:
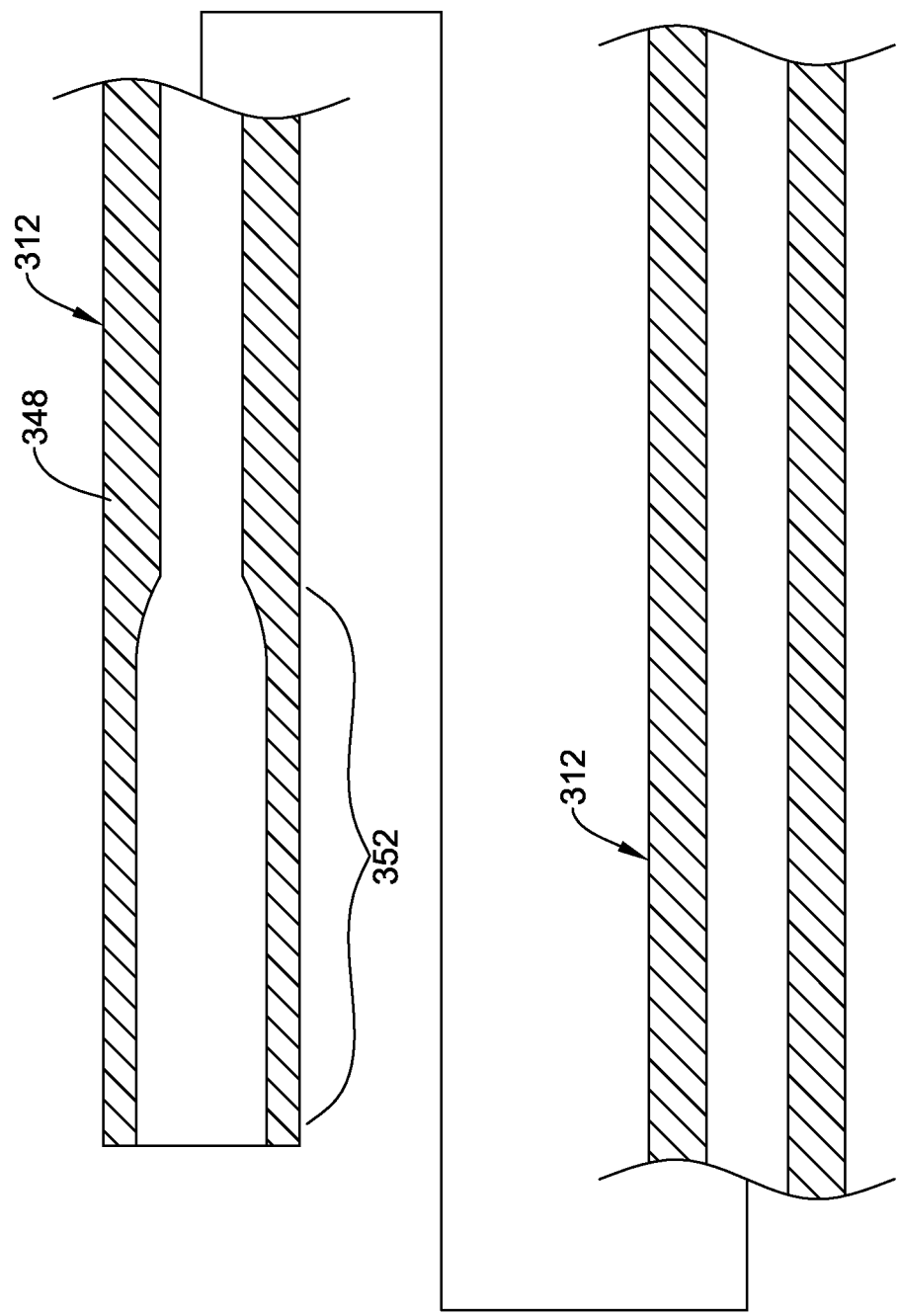

FIGS. 6-10 schematically illustrate a portion of an example method for manufacturing guidewire 300. For example, FIG. 6 illustrates tubular member 312. As indicated above, tubular member 312 may be single monolith of material or may include two or more sections joined together. Distal portion 348 of tubular member 312 may be honed or drilled to define housing region 352 as shown in FIG. 7. In general, this may include disposing a drill (e.g., a suitable drill bit) into the distal end of distal portion 348. In doing so, a portion of the wall of tubular member 312 is removed to define housing region 352. As can be seen, distal portion 348 of tubular member 312 at housing region 352 may have a reduced wall thickness and an increased inner diameter.

Figure 8:
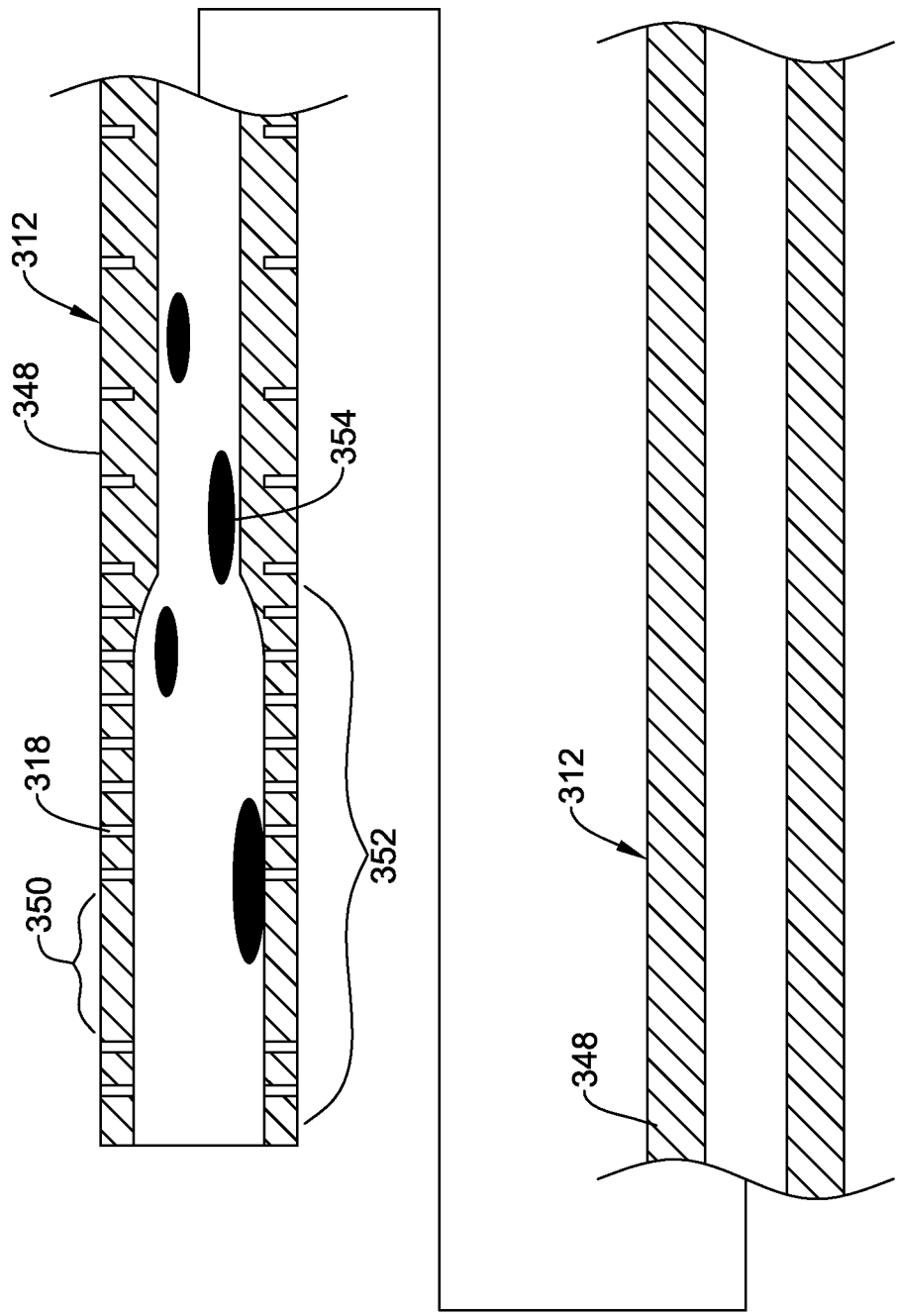

Slots 318 may be cut into distal portion 318 of tubular member 312 as shown in FIG. 8. This may include a suitable cutting process such as a laser cutting process, mechanical or micromachining process, or the like. As indicated above, the cutting process may be utilized to arrange slots 318 along distal portion 348 of tubular member 312 in the desired pattern and/or configuration. This may include defining landing region 350 (e.g., which may be free of slots 318).

Figure 9:
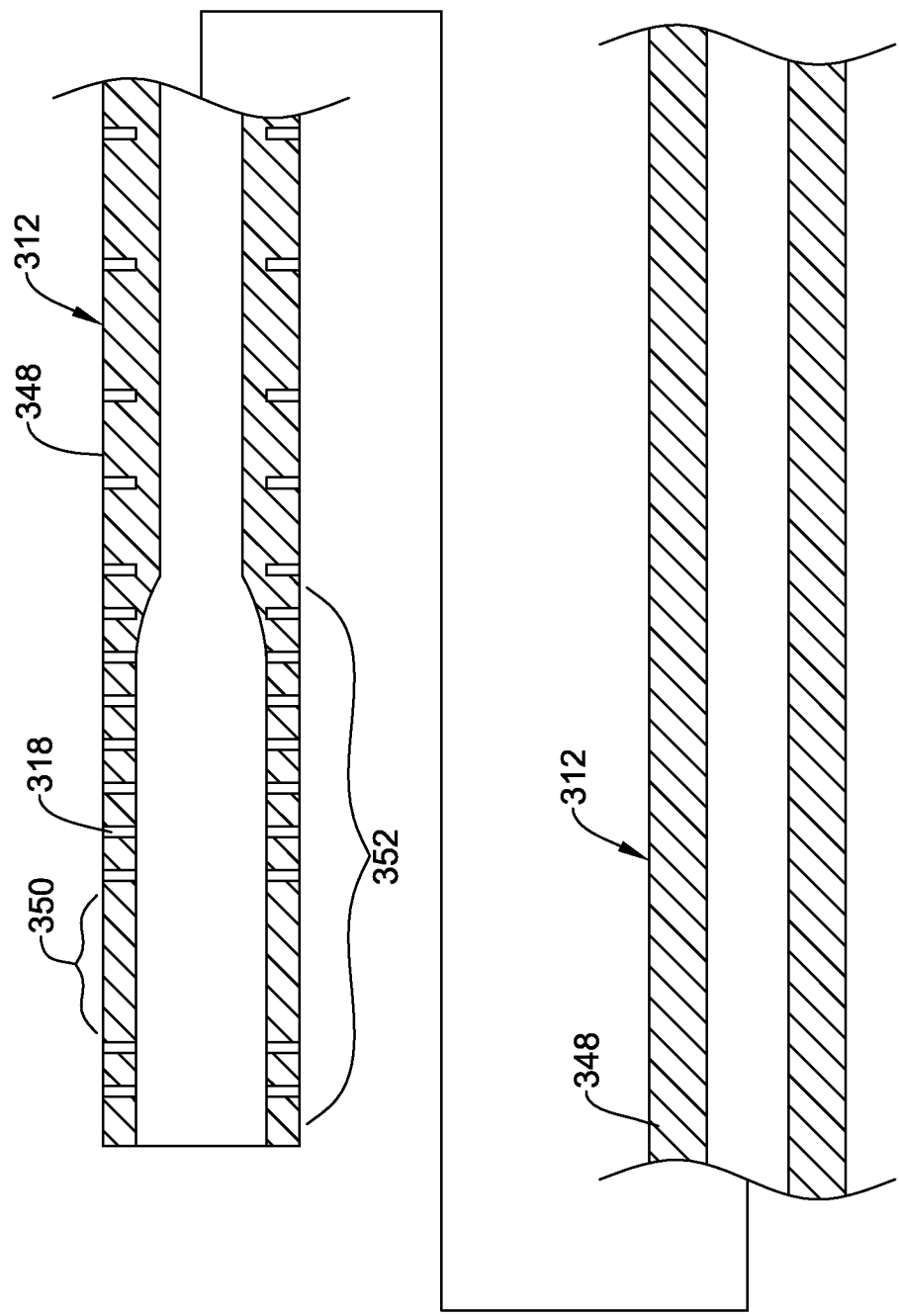

The cutting process may leave behind traces of removed material or dross 354 adjacent to slots 318, along the inner and/or outer surface of tubular member 312, or the like. Dross 354 can be removed via a cleaning and/or etching process (e.g., a chemical etching process) as schematically shown in FIG. 9.

Figure 10:
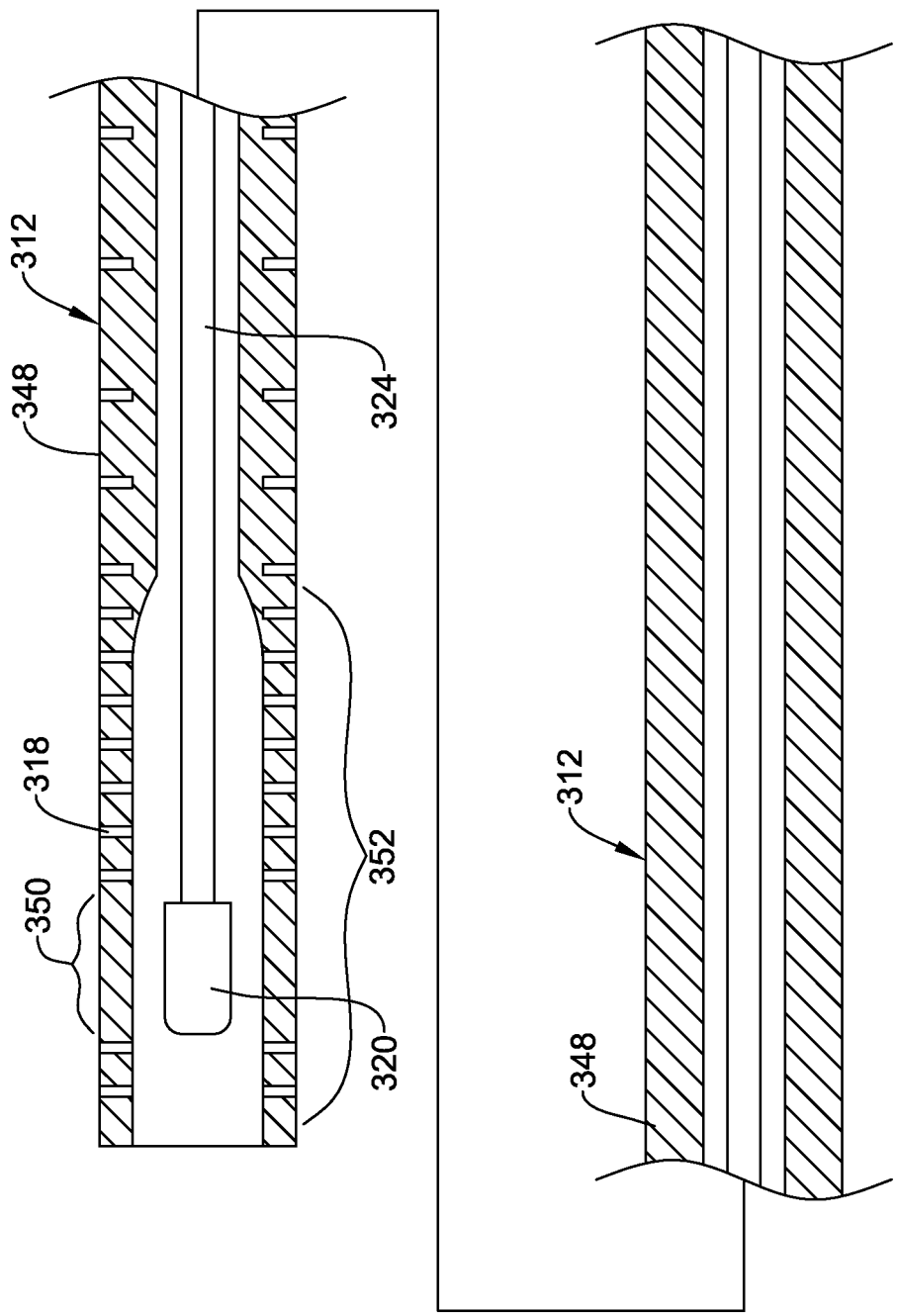

When suitable prepared/cleaned, pressure sensor 320 and optical fiber 324 may be inserted into tubular member 312 (e.g., via the distal end of tubular member 312) as shown in FIG. 10. Optical fiber 324 may be secure to tubular member 312 at one or more locations. This may include securing optical fiber 324 with a suitable adhesive or joining member (and/or the like).

Figure 11:
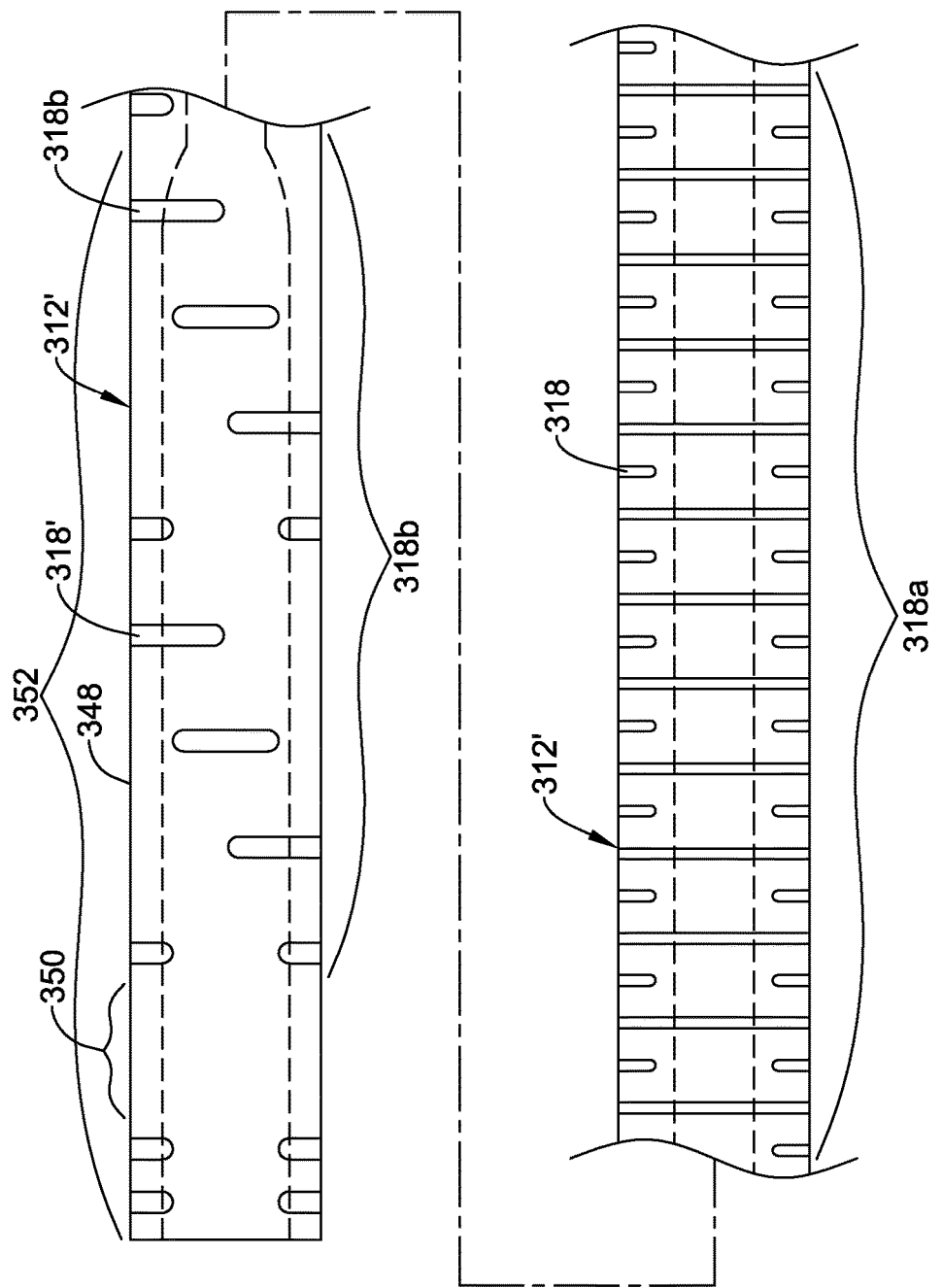
FIG. 11 is a cross-sectional side view of an example tubular member.

FIGS. 11-12 illustrate tubular member 312', showing additional details of some of the patterns contemplated for slots 318. These patterns/configurations may be utilized in guidewire 300 (e.g., with pressure sensor 320, optical fiber 324, etc.). For example, a first slot region 318a may be defined in distal portion 348 where the slots 318 are substantially evenly distributed. In other words, slots 318 may be arranged as opposed pairs of slots 318 that are longitudinally distributed along distal portion 348. A second slot region 318b may also be defined where the stiffness of tubular member 312' may be altered by altering the distribution of slots 318. Second slot region 318b may be disposed adjacent to housing region 352. Along second slot region 318b, the spacing between adjacent pairs of slots 318 may vary. This may include increased spacing, decreased spacing, or both. For example, along housing region 352 (where a portion of tubular member 312 is removed, fewer slots 318 may be needed to provide the desired flexibility. Thus, along housing region 352, the spacing between slots 318 may be increased (e.g., with fewer slots per unit area) in the distal direction. These are just examples. Numerous additional slot arrangements and/or patterns are contemplated.

In addition, some of the slots 318' positioned along housing region 352 may be widened or enlarged. These "widened" slots 318' may be generally wider than slots 318. In at least some embodiments, widened slots 318' may provide a desired level of flexibility. In addition, widened slots 318' may be positioned adjacent to landing region 350 (e.g., just distal of landing region 350) so as to provide a slightly wider opening for fluid to flow into and access pressure sensor 320. Furthermore, widened slots 318' may also help to reduce stress concentrations in the thinner wall areas along housing region 352.

The materials that can be used for the various components of guidewire 10 (and/or other guidewires disclosed herein including guidewire 300) and the various tubular members disclosed herein may include those commonly associated with medical devices. For simplicity purposes, the following discussion makes reference to tubular member 12 and other components of guidewire 10. However, this is not intended to limit the devices and methods described herein, as the discussion may be applied to other similar tubular members and/or components of tubular members or devices disclosed herein.

Tubular member 12 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of tubular member 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MRI) compatibility is imparted into guidewire 10. For example, tubular member 12 or portions thereof may be made of a material that does not substantially distort the image and create substantial artifacts (i.e., gaps in the image). Certain ferromagnetic materials, for example, may not be suitable because they may create artifacts in an MRI image. Tubular member 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of tubular member 12 that may define a generally smooth outer surface for guidewire 10. In other embodiments, however, such a sheath or covering may be absent from a portion of all of guidewire 10, such that tubular member 12 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the guidewire 10 (including, for example, the exterior surface of tubular member 12) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of tubular member 12, or other portions of guidewire 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

Various embodiments of arrangements and configurations of slots are also contemplated that may be used in addition to what is described above or may be used in alternate embodiments. For simplicity purposes, the following disclosure makes reference to guidewire 10, slots 18, and tubular member 12. However, it can be appreciated that these variations may also be utilized for other slots and/or tubular members. In some embodiments, at least some, if not all of slots 18 are disposed at the same or a similar angle with respect to the longitudinal axis of tubular member 12. As shown, slots 18 can be disposed at an angle that is perpendicular, or substantially perpendicular, and/or can be characterized as being disposed in a plane that is normal to the longitudinal axis of tubular member 12. However, in other embodiments, slots 18 can be disposed at an angle that is not perpendicular, and/or can be characterized as being disposed in a plane that is not normal to the longitudinal axis of tubular member 12. Additionally, a group of one or more slots 18 may be disposed at different angles relative to another group of one or more slots 18. The distribution and/or configuration of slots 18 can also include, to the extent applicable, any of those disclosed in U.S. Pat. Publication No. US 2004/0181174, the entire disclosure of which is herein incorporated by reference.

Slots 18 may be provided to enhance the flexibility of tubular member 12 while still allowing for suitable torque transmission characteristics. Slots 18 may be formed such that one or more rings and/or tube segments interconnected by one or more segments and/or beams that are formed in tubular member 12, and such tube segments and beams may include portions of tubular member 12 that remain after slots 18 are formed in the body of tubular member 12. Such an interconnected structure may act to maintain a relatively high degree of torsional stiffness, while maintaining a desired level of lateral flexibility. In some embodiments, some adjacent slots 18 can be formed such that they include portions that overlap with each other about the circumference of tubular member 12. In other embodiments, some adjacent slots 18 can be disposed such that they do not necessarily overlap with each other, but are disposed in a pattern that provides the desired degree of lateral flexibility.

Additionally, slots 18 can be arranged along the length of, or about the circumference of, tubular member 12 to achieve desired properties. For example, adjacent slots 18, or groups of slots 18, can be arranged in a symmetrical pattern, such as being disposed essentially equally on opposite sides about the circumference of tubular member 12, or can be rotated by an angle relative to each other about the axis of tubular member 12. Additionally, adjacent slots 18, or groups of slots 18, may be equally spaced along the length of tubular member 12, or can be arranged in an increasing or decreasing density pattern, or can be arranged in a non-symmetric or irregular pattern. Other characteristics, such as slot size, slot shape, and/or slot angle with respect to the longitudinal axis of tubular member 12, can also be varied along the length of tubular member 12 in order to vary the flexibility or other properties. In other embodiments, moreover, it is contemplated that the portions of the tubular member, such as a proximal section, or a distal section, or the entire tubular member 12, may not include any such slots 18.

As suggested herein, slots 18 may be formed in groups of two, three, four, five, or more slots 18, which may be located at substantially the same location along the axis of tubular member 12. Alternatively, a single slot 18 may be disposed at some or all of these locations. Within the groups of slots 18, there may be included slots 18 that are equal in size (i.e., span the same circumferential distance around tubular member 12). In some of these as well as other embodiments, at least some slots 18 in a group are unequal in size (i.e., span a different circumferential distance around tubular member 12). Longitudinally adjacent groups of slots 18 may have the same or different configurations. For example, some embodiments of tubular member 12 include slots 18 that are equal in size in a first group and then unequally sized in an adjacent group. It can be appreciated that in groups that have two slots 18 that are equal in size and are symmetrically disposed around the tube circumference, the centroid of the pair of beams (i.e., the portion of tubular member 12 remaining after slots 18 are formed therein) is coincident with the central axis of tubular member 12. Conversely, in groups that have two slots 18 that are unequal in size and whose centroids are directly opposed on the tube circumference, the centroid of the pair of beams can be offset from the central axis of tubular member 12. Some embodiments of tubular member 12 include only slot groups with centroids that are coincident with the central axis of the tubular member 12, only slot groups with centroids that are offset from the central axis of tubular member 12, or slot groups with centroids that are coincident with the central axis of tubular member 12 in a first group and offset from the central axis of tubular member 12 in another group. The amount of offset may vary depending on the depth (or length) of slots 18 and can include other suitable distances.

Slots 18 can be formed by methods such as micromachining, saw-cutting (e.g., using a diamond grit embedded semiconductor dicing blade), electron discharge machining, grinding, milling, casting, molding, chemically etching or treating, or other known methods, and the like. In some such embodiments, the structure of the tubular member 12 is formed by cutting and/or removing portions of the tube to form slots 18. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 110 may include forming slots 18 tubular member 12 using these or other manufacturing steps.

In at least some embodiments, slots 18 may be formed in tubular member using a laser cutting process. The laser cutting process may include a suitable laser and/or laser cutting apparatus. For example, the laser cutting process may utilize a fiber laser. Utilizing processes like laser cutting may be desirable for a number of reasons. For example, laser cutting processes may allow tubular member 12 to be cut into a number of different cutting patterns in a precisely controlled manner. This may include variations in the slot width, ring width, beam height and/or width, etc. Furthermore, changes to the cutting pattern can be made without the need to replace the cutting instrument (e.g., blade). This may also allow smaller tubes (e.g., having a smaller outer diameter) to be used to form tubular member 12 without being limited by a minimum cutting blade size. Consequently, tubular member 12 may be fabricated for use in neurological devices or other devices where a relatively small size may be desired.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A pressure sensing guidewire, comprising:
   a tubular member having a proximal portion and a distal portion;
   wherein the distal portion has a plurality of slots formed therein;
   wherein the distal portion has a first wall thickness along a first region and a second wall thickness different from the first wall thickness along a second region;
   wherein the first region has a first inner diameter, wherein the second region has a second inner diameter, and wherein the first inner diameter is greater than the second inner diameter;
   wherein the tubular member has a constant outer diameter along a transition section where the first region transitions to the second region, along at least a first section of the first region, and along at least a second section of the second region; and
   a pressure sensor disposed within the distal portion of the tubular member along the first region.

2. The pressure sensing guidewire of claim 1, wherein the pressure sensor is an optical pressure sensor.

3. The pressure sensing guidewire of claim 1, wherein the pressure sensor is a fabry-perot pressure sensor.

4. The pressure sensing guidewire of claim 1, wherein a fiber optic cable is attached to the pressure sensor and extends proximally thererfrom.

5. The pressure sensing guidewire of claim 1, wherein the plurality of slots include at least a pair of slots lying in a plane transverse to a longitudinal axis of the tubular member.

6. The pressure sensing guidewire of claim 1, wherein the slots have a first slot density along the first region of the distal portion of the tubular member and a second slot density different from the first slot density along the second region of the distal portion of the tubular member.

7. The pressure sensing guidewire of claim 1, wherein the first wall thickness is greater than the second wall thickness.

8. The pressure sensing guidewire of claim 7, wherein the first region is disposed distally of the second region.

9. The pressure sensing guidewire of claim 7, wherein the pressure sensor is disposed along the first region.

10. The pressure sensing guidewire of claim 7, wherein at least some of the slots disposed adjacent to the first region have an enlarged slot width relative to the slots disposed along the second region.

11. The pressure sensing guidewire of claim 7, wherein the first region includes a landing portion that is free of slots and wherein the pressure sensor is disposed adjacent to the landing portion.

12. The pressure sensing guidewire of claim 1, wherein the tubular member has a substantially constant outer diameter.

13. The pressure sensing guidewire of claim 1, wherein the distal portion of the tubular member is formed from a first tube and wherein the proximal portion of the tubular member is formed from a second tube different from the first tube.

14. The pressure sensing guidewire of claim 13, wherein the first tube includes MP-35N.

15. A pressure sensing guidewire, comprising:
a tubular member having a proximal portion, a distal portion, and a lumen defined therein;
wherein the tubular member has a constant outer diameter;
wherein the distal portion has a first region having a first wall thickness and having a first inner diameter, wherein the distal portion has and a second region with a second wall thickness that is larger than the first wall thickness and has a second inner diameter smaller than the first inner diameter;
wherein the distal portion has a plurality of slots formed therein;
wherein at least some of the slots disposed along the first region have an increased slot width relative to slots disposed along the second region;
wherein the first region includes a landing area that is free of slots; and
a pressure sensor disposed along the first region and positioned adjacent to the landing area.

16. A method for manufacturing a pressure sensing guidewire, the method comprising:
drilling a distal portion of a tubular member so as to define a thinned wall region having a reduced wall thickness and an increased inner diameter;
wherein the tubular member has a constant outer diameter along the distal portion and along at least a portion of the tubular member extending proximally from the distal portion;
forming a plurality of slots in the distal portion; and
disposing an optical pressure sensor along the thinned wall region of the distal portion.

17. The method of claim 16, wherein the slots have a slot density that varies along the length of the distal portion of the tubular member.

18. The method of claim 16, wherein at least some of the slots disposed along the thinned wall region have an increased slot thickness relative to other slots disposed along the distal portion.

19. The method of claim 16, wherein the thinned wall region includes a landing portion that is free of slots and wherein the optical pressure sensor is disposed adjacent to the landing portion.

20. The method of claim 16, wherein the distal portion of the tubular member is formed from a first tube and wherein the proximal portion of the tubular member is formed from a second tube different from the first tube.

\* \* \* \* \*